United States Patent [19]

Barger et al.

[11] Patent Number: 5,510,559

[45] Date of Patent: Apr. 23, 1996

[54] SELECTIVITY IN HYDROCARBON CONVERSION

[75] Inventors: Paul T. Barger, Arlington Heights; Dorothy M. Richmond, La Grange Park; Patrick T. Darby, II, Naperville; R. Joe Lawson, Arlington Heights, all of Ill.

[73] Assignee: UOP, Des Plaines, Ill.

[21] Appl. No.: 245,183

[22] Filed: May 17, 1994

[51] Int. Cl.$^6$ .................................................. C07C 5/22
[52] U.S. Cl. .................................... 585/664; 585/671
[58] Field of Search ........................... 585/664, 671

[56] References Cited

U.S. PATENT DOCUMENTS

| | | | |
|---|---|---|---|
| 4,440,871 | 4/1984 | Lok et al. | 502/214 |
| 4,508,836 | 4/1985 | Haag et al. | 502/53 |
| 4,567,029 | 1/1986 | Wilson et al. | 423/306 |
| 4,741,820 | 5/1988 | Coughlin et al. | 208/138 |
| 4,758,419 | 7/1988 | Lok et al. | 423/306 |
| 4,793,984 | 12/1988 | Lok et al. | 423/306 |
| 4,861,938 | 8/1989 | Lewis et al. | 585/640 |
| 5,107,050 | 4/1992 | Gaffney et al. | 585/671 |
| 5,132,484 | 7/1992 | Gajda | 585/667 |
| 5,234,875 | 8/1993 | Han et al. | 502/77 |
| 5,321,184 | 6/1994 | Low et al. | 585/481 |
| 5,346,611 | 9/1994 | Coughlin et al. | 208/138 |
| 5,365,008 | 11/1994 | Burger et al. | 585/671 |

*Primary Examiner*—Asok Pal
*Assistant Examiner*—Bekir L. Yildirim
*Attorney, Agent, or Firm*—Thomas K. McBride; John F. Spears, Jr.; Richard E. Conser

[57] ABSTRACT

An improved process is disclosed for the conversion of hydrocarbons, using a catalyst comprising a non-zeolitic molecular sieve which has been activity-moderated by controlled carbon deposition. It is of particular interest in skeletal isomerization to increase the proportion of olefins containing tertiary carbons in the product with low formation of undesirable by-products. Controlled carbon deposition increases selectivity to the desired olefin isomers. Product olefins may be further processed to obtain ethers, which enjoy high current interest as components for reformulated gasoline.

9 Claims, 2 Drawing Sheets

SELECTIVITY IN HYDROCARBON CONVERSION

FIELD OF THE INVENTION

This invention relates to an improved process for the conversion of hydrocarbons. More specifically, the invention concerns treating of a molecular-sieve catalyst to increase its selectivity prior to its use for hydrocarbon conversion.

GENERAL BACKGROUND AND RELATED ART

Molecular-sieve catalysts are commonly utilized to upgrade petroleum fractions and to produce a variety of petrochemical products. Reactions such as cracking, hydrocracking, reforming, isomerization of aromatics and aliphatics, polymerization, alkylation, dealkylation, transalkylation and disproportionation are effectively and efficiently promoted by catalysts featuring molecular sieves. The most widely used of the molecular sieves are the crystalline aluminosilicate zeolites formed from corner-sharing $AlO_2$ and $SiC_2$ tetrahedra. The zeolites generally feature pore openings of uniform dimensions, significant ion-exchange capacity and the capability of reversibly desorbing an adsorbed phase which is dispersed throughout the internal voids of the crystal without displacing any atoms which make up the permanent crystal structure. Catalytic properties of zeolites, e.g., acidic activity and shape selectivity, are controlled by such parameters as selection of zeolite type and pore dimensions, crystal size, silica/alumina ratio, and the nature of cations used to balance the electrovalence of tetrahedral aluminum.

Methods have been disclosed for modifying the catalytic activity of zeolites in defined process uses. U.S. Pat. No. 4,508,836 (Haag et al.) teaches a process for converting an aromatic-containing feedstock using a crystalline aluminosilicate zeolite which has been precoked. Oligomerization of olefins using a crystalline silicate which has been surface-inactivated by steaming and coking is disclosed in U.S. Pat. No. 5,234,875 (Han et al.). Patent application Ser. No. 997,831 discloses high-severity followed by moderate-severity $C_8$-aromatics isomerization.

More recently, a class of useful non-zeolitic molecular sieves containing framework tetrahedral units ($TO_2$) of aluminum ($AlO2$), phosphorus ($PO_2$) and at least one additional element EL ($ELO_2$) has been disclosed. "Non-zeolitic molecular sieves" or "NZMS" include the "SAPO" molecular sieves of U.S. Pat. No. 4,440,871 (Lok et al.), "ELAPSO" molecular sieves as disclosed in U.S. Pat. No. 4,793,984 (Lok et al.), "MgAPSO" sieves of U.S. Pat. No. 4,758,419 (Lok et al.) and crystalline metal aluminophosphates—MeAPOs where "Me" is at least one of Mg, Mn, Co and Zn—as disclosed in U.S. Pat. No. 4,567,029 (Wilson et al.). Framework As, Be, B, Cr, Fe, Ga, Ge, Li, Ti or V and binary metal aluminophosphates are disclosed in various species patents. U.S. Pat. No. 4,861,938 discloses light-olefin production over a NZMS catalyst with catalyst deactivation, at least partial regeneration and further conditioning of the catalyst with a basic material.

The use of an NZMS-containing catalyst for the isomerization of butenes is disclosed in U.S. Pat. No. 5,132,484 (Gajda). U.S. Pat. No. 5,107,050 (Gaffney et al.), discloses butene isomerization using a MgAPSO or SAPO molecular sieve at a temperature above 900° F.

Non-zeolitic molecular sieves as used in catalysts have unique characteristics of pore dimension, acidity, etc. which affect activity and selectivity in certain hydrocarbon-conversion applications. One problem facing workers in the art is how to moderate and control activity over the life of the catalyst to obtain favorable results.

SUMMARY OF THE INVENTION

It is an object of the present invention to provide an improved process for the conversion of hydrocarbons. A corollary objective of the invention is to improve selectivity in an olefin isomerization process.

This invention is based on the discovery that a catalytic isomerization process using a catalyst comprising at least one NZMS and which has been activity-moderated by controlled carbon deposition demonstrates surprising efficiency in converting normal butene to isobutene.

A broad embodiment of the present invention is directed to the catalytic conversion of hydrocarbons using a non-zeolitic molecular sieve, or "NZMS," catalyst that has been activity-moderated by controlled carbon deposition. The activity moderation is effected using a reactive organic compound, preferably a hydrocarbon feedstock to the catalytic conversion step. In an alternative embodiment, the controlled carbon deposition is carried out in the absence of free hydrogen.

One favored embodiment of hydrocarbon conversion is skeletal isomerization of olefinic hydrocarbons using an NZMS catalyst, preferably accomplishing activity moderation using the olefinic-hydrocarbon isomerization feedstock. In a highly preferred embodiment, the feedstock to catalytic isomerization comprises principally butenes and catalytic isomerization increases the concentration of isobutene in the product. An alternative preferred embodiment comprises the isomerization of linear pentenes to isopentene, optionally in combination with butene isomerization.

In another aspect, the non-zeolitic molecular sieve of the hydrocarbon-conversion catalyst comprises silicoaluminophosphates or "SAPO."

These as well as other objects and embodiments will become apparent from the detailed description of the invention.

DESCRIPTION OF THE PREFERRED EMBODIMENTS

Figure 1:
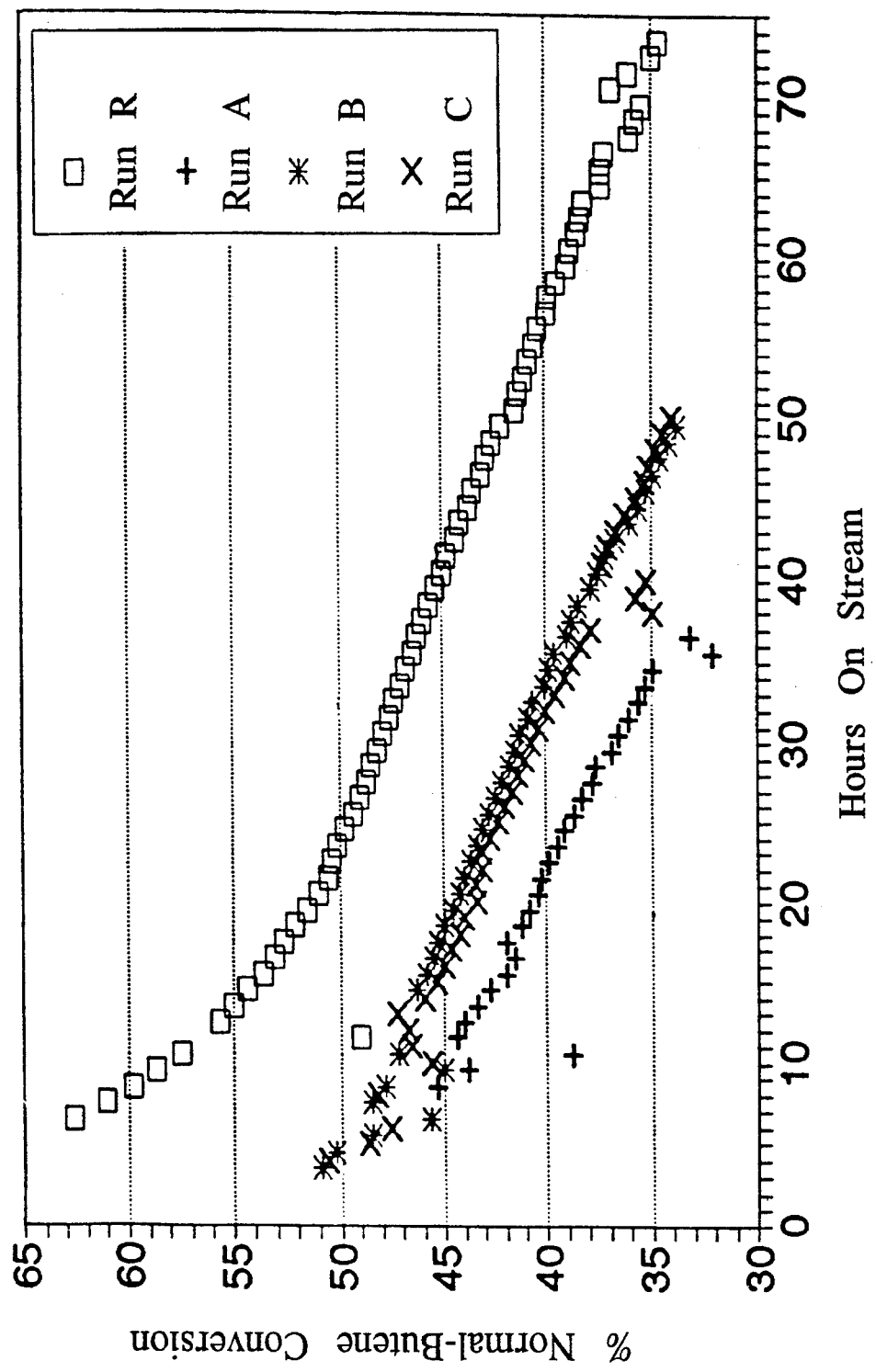
FIG. 1 shows n-butene conversion vs. time on-stream for butene skeletal isomerization using catalysts with and without activity moderation by controlled carbon deposition.

Hydrocarbons are converted according to the present invention using an activity-moderated catalyst containing at least one non-zeolitic molecular-sieve ("NZMS") to obtain a converted product. The sieves preferably are composited with an inorganic-oxide binder, and optionally may contain one or more metals as described herein, to obtain the hydrocarbon-conversion catalyst. A hydrocarbon feedstock is converted at hydrocarbon-conversion conditions including a pressure of about atmospheric to 200 atmospheres, temperatures of about 50° to 600° C., liquid hourly space velocities of from about 0.1 to 100 $hr^{-1}$, and, if hydrogen is present, hydrogen-to-hydrocarbon molar ratios of from about 0.1 to 80. Hydrocarbon-conversion processes employing such catalysts and conditions include isomerization, reforming, dehydrocyclization, dehydrogenation, disproportionation, transalkylation, dealkylation, alkylation, polymerization, hydrocracking and catalytic cracking.

Reforming processes of the present invention use a NZMS catalyst which preferably contains a hydrogenation promoter such as a platinum-group metal, optionally one or more modifiers such as rhenium and Group IVA (14) metals, and an inorganic-oxide binder. Hydrocarbon feedstocks, preferably naphtha, contact the catalyst at pressures of between atmospheric and 40 atmospheres, temperatures of about 350° to 600° C., liquid hourly space velocities (LHSV) from 0.2 to 20 $hr^{-1}$, and hydrogen-to-hydrocarbon molar ratios of from about 0. 1 to 10. Further details are provided in U.S. application Ser. No. 08/086,961, incorporated by reference. Dehydrocyclization of naphthas and other paraffin-containing stocks is carried out over a similar catalyst, preferably nonacidic through incorporation of an alkali or alkaline earth metal, at similar conditions with operating pressure no higher than about 15 atmospheres. Products of reforming and dehydrocyclization generally have an increased concentration of aromatics relative to the feedstocks.

Isomerization of light hydrocarbons according to the present invention is advantageously effected using NZMS catalyst compositions within the scope of those described for use in reforming processes. The light hydrocarbon feedstock contacts the catalyst at pressures of between atmospheric and 70 atmospheres, temperatures of about 50° to 300°, LHSV from 0.2 to 5 $hr^{-1}$, and hydrogen-to-hydrocarbon molar ratios of from about 0.1 to 5. Isomerization of olefins such as butenes, pentenes and higher olefins is effected over a catalyst which preferably does not contain a substantial hydrogenation component, in order to avoid olefin hydrogenation, at somewhat higher temperatures of 200° to 600° C. and higher space velocities of 0.5 to 100 $hr^{-1}$. Usually isomerization yields a product having a greater concentration of branched hydrocarbons.

Heavier paraffins, waxy distillates and raffinates are isomerized to increase the branching of the hydrocarbons using essentially the same catalyst compositions as used in reforming. Operating conditions include pressures of between about 20 and 150 atmospheres, temperatures of about 200° to 450° C., LHSV from 0.2 to 10 $hr^{-1}$, and hydrogen-to-hydrocarbon molar ratios of from about 0.5 to 10.

Hydrocracking processes use NZMS catalyst compositions of the present invention which preferably contain a hydrogenation promoter such as one or more of Group VIII (8–10) and Group VIB (6) metals and an inorganic-oxide matrix. A variety of feedstocks including atmospheric and vacuum distillates, cycle stocks and residues are cracked to yield lighter products at pressures of between 30 and 200 atmospheres, temperatures of about 200° to 450° C., LHSV from 0.1 to 10 $hr^{-1}$, and hydrogen-to-hydrocarbon molar ratios of from about 2 to 80.

Catalyst compositions of the same general description as those used in hydrocracking processes are useful in hydrotreating and hydrofining. A variety of naphthas, atmospheric and vacuum distillates, cracked and cycle stocks and residues are treated to remove sulfur, nitrogen and other heteroatoms and to saturate unsaturates at pressures of between 30 and 150 atmospheres, temperatures of about 200° to 450° C., LHSV from 0.1 to 20 $hr^{-1}$, and hydrogen-to-hydrocarbon molar ratios of from about 2 to 20. Operating conditions vary with respect to the difficulty of heteroatom removal, usually relating to the size and aromaticity of the heteroatom-containing molecules, and the concentration particularly of nitrogen in the feedstock. Products meet environmental requirements, are not as corrosive or contaminating of downstream equipment, or effect less deactivation of catalysts in downstream-processing units relative to the feedstock.

Disproportionation and transalkylation suitably are effected with NZMS catalyst compositions as disclosed in relation to reforming processes. Suitable feedstocks include single-ring aromatics, naphthalenes and light olefins, and the reaction yields more valuable products of the same hydrocarbon specie. Isomerization also may occur at the operating conditions of between 10 and 70 atmospheres, temperatures of about 200° to 500° C., and LHSV from 0.1 to 10 $hr^{-1}$. Hydrogen is optionally present at a molar ratio to hydrocarbon of from about 0.1 to 10.

Activity moderation according to the invention is favorably applied in the use of NZMS in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example, ortho-xylene, meta-xylene, para-xylene, ethylbenzene, ethyltoluenes, trimethylbenzenes, diethylbenzenes, triethyl-benzenes, methylpropylbenzenes, ethylpropylbenzenes, diisopropylbenzenes, and mixtures thereof.

Isomerization of a $C_8$-aromatic mixture containing ethylbenzene and xylenes is the preferred alkylaromatic-isomerization use of the present invention. Generally the $C_8$ aromatics comprise a non-equilibrium mixture; i.e., at least one $C_8$-aromatic isomer is present in a concentration that differs substantially from the equilibrium concentration at isomerization conditions, usually pursuant to removal of para- and/or ortho-xylene from a fresh $C_8$ aromatic mixture obtained from an aromatics-production process.

The alkylaromatic charge stock, preferably a non-equilibrium mixture of $C_8$ aromatics, is contacted with a catalytic combination as hereinbefore described in an isomerization zone while maintaining the zone at appropriate alkylaromatic-isomerization conditions. The conditions employed in a $C_8$-aromatic isomerization zone comprise a temperature ranging from about 0° to 600° C. or more, preferably is in the range of from about 300° to 500° C.; a pressure generally from about 1 to 100 atmospheres absolute, preferably less than about 50 atmospheres; and a liquid hourly space velocity of charge stock of from about 0.1 to 30 $hr^{-1}$, and preferably 0.5 to 10 $hr^{-1}$. The hydrocarbon charge stock optimally is reacted in admixture with hydrogen at a hydrogen/hydrocarbon mole ratio of about 0.5:1 to about 25:1 or more; other inert diluents such as nitrogen, argon and light hydrocarbons may be present.

A highly preferred use of the present invention is in the skeletal isomerization of olefins with a NZMS catalyst. In the group of olefinic hydrocarbons suitable as feedstock to the catalytic isomerization process of the present invention, mono-olefins having from 4 to 10 carbon atoms per molecule are preferred. Feedstock olefins may be contained in product streams from petroleum-refining, synthetic-fuel, or petrochemical operations, especially in raffinate from an etherification process. The mono-olefins should be present in the feedstock in a concentration of from about 0.5 to 100 mass %, and preferably from about 5 to 100 mass %, with most of the balance usually comprising paraffins. Butenes are especially preferred, particularly in a feedstock rich in one or more of the linear butenes, i.e., 1-butene, cis-2-butene and trans-2-butene, if isobutene is the desired product. An advantageous alternative feedstock within the group of preferred olefins comprises pentenes, often designated amylenes, comprising one or both of the linear pentenes 1-pentene and 2-pentene which are isomerized to one or more of the isopentenes 2-methyl-2-butene, 2-methyl-1-butene, and 3-methyl-1-butene. The feedstock to the present process may advantageously contain both butenes and pentenes.

Isomerization of olefins in the feedstock is effected at conditions including reaction temperatures generally in the range of about 50° to 750° C. and for the isomerization of butenes in the range of 200° to 600° C.; pentene isomerization is advantageously performed at temperatures in the range of about 200° to 500° C. Reactor operating pressures usually will range from about atmospheric to 50 atmospheres. The amount of catalyst in the reactors will provide an overall weight hourly space velocity of from about 0.5 to 100 $hr^{-1}$, and preferably from about 1 to 40 $hr^{-1}$. An olefinic feedstock may contact the catalyst in the absence of hydrogen or in presence of hydrogen in a molar ratio to feedstock of from about 0.01 to about 10.

Activity moderation by controlled carbon deposition suitably may be effected using one or more of a variety of reactive organic compounds including hydrocarbons, oxygenates, and nitrogen- and sulfur-containing compounds, with hydrocarbons such as paraffins, naphthenes, olefins, aromatics and polycyclics being preferred. Activity-moderation operating conditions are chosen generally within the broad ranges of the specified hydrocarbon-conversion application in order to use the same equipment for activity moderation as for conversion, with relatively higher temperature, higher pressure, and/or lower ratio of free hydrogen (if present) to the reactive organic compound than are used in the subsequent hydrocarbon processing. Activity moderation by controlled carbon deposition is carried out over a period of about 0.1 to 24 hours to effect a catalyst carbon content of about 0.1 to 20 mass %, until the desired hydrocarbon-conversion performance is obtained following the activity-moderation procedure. If the hydrocarbons used to effect controlled deposition of carbon on the catalyst are substantially the same as the feedstock to hydrocarbon conversion, contacting of the catalyst optimally then is continued at hydrocarbon-conversion conditions; i.e., contacting of the feedstock at activity-moderation and at hydrocarbon-conversion conditions optimally is effected sequentially without an intervening step.

The selectivity of the preferred olefin isomerization process is enhanced through such controlled carbon deposition, thus enhancing the product value of the process. It is believed, without limiting the invention, that olefin isomerization without activity moderation results in an adverse effect on the catalyst during the first portion of the isomerization operation when the catalyst is fresh and highly active; high conversion during this period could result in loss of selectivity.

Activity moderation by controlled carbon deposition in an olefin-isomerization process preferably is effected using hydrocarbons such as paraffins, naphthenes, olefins, aromatics and polycyclics, with the olefin-containing feedstock to the isomerization operation being especially preferred. If the isomerization feedstock is used for to effect controlled deposition of carbon on the catalyst, feedstock contacting of the catalyst optimally then is continued at isomerization conditions; i.e., contacting of the feedstock at activity-moderation and at isomerization conditions optimally is effected sequentially without an intervening step.

Activity-moderation operating conditions are chosen to improve subsequent isomerization performance. Relative to isomerization conditions, one or more of the following may be effective for controlled deposition of carbon: higher temperature, lower space velocity, higher pressure, and/or lower ratio of free hydrogen to the reactive organic compound. Activity-moderation temperature ranges from about 200° to 600° C., preferably from about 400° to 600° C., with a range of 400° to 510° C. being especially preferred. Operating pressure is between about atmospheric and 50 atmospheres absolute, with a preferred range of atmospheric to 10 atmospheres. Weight hourly space velocity generally is between about 0.5 and 100 $hr^{-1}$, and preferably from about 1 to 40 $hr^{-1}$. The activity moderation may be carried out in the absence of free hydrogen, or hydrogen may be present in a molar ratio to the feedstock of about 0.01 to 5.

Activity moderation by controlled carbon deposition is carried out over a period of about 0.1 to 24 hours, and preferably about 0.5 to 6 hours. In some instances a very short period of activity moderation, e.g., about 0.1 to 0.5 hours, provides useful results. Activity moderation is continued until the desired olefin-isomerization performance is obtained following the activity-moderation procedure. The sufficiency of activity moderation may be determined during approximately the first three hours of the subsequent isomerization operation by observing reduced conversion of olefins in the feedstock relative to such conversion at equivalent conditions without catalyst activity moderation. The reduction in olefin conversion may be about 1 to 50%, more usually 5 to 30%. The conclusion of activity moderation also may be determined by catalyst carbon content, which may vary according to parameters such as but not limited to feedstock type, conversion objectives and the nature and condition of the catalyst. Generally the carbon content of the catalyst is about 0.1 to 20 mass % of the catalyst, and more usually 0.5 to 5 mass %.

Activity moderation is applied to catalysts containing at least one non-zeolitic molecular sieve, also characterized as "NZMS" and defined in the instant invention to include molecular sieves containing framework tetrahedral units ($TO_2$) of aluminum ($AlO_2$), phosphorus ($PO_2$) and at least one additional element (EL) as a framework tetrahedral unit ($ELO_2$). "NZMS" includes the "SAPO" molecular sieves of U.S. Pat. No. 4,440,871, "ELAPSO" molecular sieves as disclosed in U.S. Pat. No. 4,793,984 and certain "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S. Pat. No. 4,567,029, crystalline ferroaluminophosphates (FAPOs) are disclosed in U.S. Pat. No. 4,554,143, titanium aluminophosphates (TAPOs) are disclosed in U.S. Pat. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, CoAPSO as disclosed in U.S. Pat. No. 4,744,970, MgAPSO as disclosed in U.S. Pat. No. 4,758,419 and MnAPSO as disclosed in U.S. Pat. No. 4,793,833. The aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMSs set forth hereinafter the mole fraction of the NZMS are defined as compositional values which are plotted in phase diagrams in each of the identified patents, published applications or copending applications.

The preferred NZMSs are the silicoaluminophosphate molecular sieves described in U.S. Pat. No. 4,440,871. The silicoaluminophosphate molecular sieves are disclosed as microporous crystalline silicoaluminophosphates, having a three-dimensional microporous framework structure of $PO_2^+$, $AlO_2^-$ and $SiO_2$ tetrahedral units, and whose essential empirical chemical composition on an anhydrous basis is:

mR:  $O_2$ wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| Point | Mole Fraction | | |
|-------|------|------|------|
|       | x    | y    | z    |
| A     | 0.01 | 0.47 | 0.52 |
| B     | 0.94 | 0.01 | 0.05 |
| C     | 0.98 | 0.01 | 0.01 |
| D     | 0.39 | 0.60 | 0.01 |
| E     | 0.01 | 0.60 | 0.39 |

The silicoaluminophosphates of U.S. Pat. No. 4,440,871 are generally referred to therein as "SAPO" as a class, or as "SAPO-n" wherein "n" is an integer denoting a particular SAPO such as SAPO-11, SAPO-31, SAPO-40 and SAPO-41. The especially preferred species SAPO-11 as referred to herein is a silicoaluminophosphate having a characteristic X-ray powder diffraction pattern which contains at least the d-spacings set forth below:

| SAPO-11 | | |
|---------|---|---|
| 2r | d | Relative Intensity |
| 9.4–9.65 | 9.41–9.17 | m |
| 20.3–20.6 | 4.37–4.31 | m |
| 21.0–21.3 | 4.23–4.17 | vs |
| 21.1–2.35 | 4.02–3.99 | m |
| 22.5–22.9 (doublet) | 3.95–3.92 | m |
| 23.15–23.35 | 3.84–3.81 | m–s |

Ferroaluminophosphates are disclosed in U.S. Pat. No. 4,554,143, incorporated herein by reference, and have a three-dimensional microporous crystal framework structure of $AlO_2$, $FeO_2$, and $PO_2$ tetrahedral units and have an essential empirical chemical composition, on an anhydrous basis, of:

mR:  $O_2$ wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y", and "z" represent the mole fractions of iron, aluminum and phosphorus, respectively, present as tetrahedral oxides, representing the following values for "x", "y", and "z":

| Point | Mole Fraction | | |
|-------|------|------|------|
|       | x    | y    | z    |
| A     | 0.01 | 0.60 | 0.39 |
| B     | 0.01 | 0.39 | 0.60 |
| C     | 0.35 | 0.05 | 0.60 |
| D     | 0.35 | 0.60 | 0.05 |

When synthesized the minimum value of "m" in the formula above is 0.02. The iron of the $FeO_2$ structural units can be in either the ferric or ferrous valence state, depending largely upon the source of the iron in the synthesis gel. Thus, an $FeO_2$ tetrahedron in the structure can have a net charge of either −1 or −2. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in an yet undetermined form and may or may not be structurally significant.

For convenience in describing the ferroaluminophosphates, the "short-hand" acronym "FAPO" is sometimes employed hereinafter. To identify the various structural species which make up the generic class FAPO, each species is assigned a number and is identified, for example, as FAPO-11, FAPO-31 and so forth.

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three-dimensional microporous crystal framework structure of $MO^{-2}_2$, $AlO^-_2$ and $PO_2+$ tetrahedral units and have an essential empirical chemical composition, on an anhydrous basis, of:

mR:  $O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are within the following limiting values for "x", "y", and "z":

|       | Mole Fraction |      |      |
| Point | x    | y    | z    |
| ----- | ---- | ---- | ---- |
| A     | 0.01 | 0.60 | 0.39 |
| B     | 0.01 | 0.39 | 0.60 |
| C     | 0.35 | 0.05 | 0.60 |
| D     | 0.35 | 0.60 | 0.05 |

When synthesized the minimum value of "m" in the formula above is 0.02.

The CoAPSO molecular sieves of U.S. Pat. No. 4,744,970 have three-dimensional microporous framework structures of $CoO_2^{-2}$, $AlO_2^{-}$, $PO_2+$ and $SiO_2$ tetrahedral units and have an empirical chemical composition on an anhydrous basis expressed by the formula:

mR: $(Co_wAl_xP_ySi_z)O_2$ wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

|       | Mole Fraction |      |         |
| Point | x    | y    | (z + w) |
| ----- | ---- | ---- | ------- |
| A     | 0.60 | 0.38 | 0.02    |
| B     | 0.38 | 0.60 | 0.02    |
| C     | 0.01 | 0.60 | 0.39    |
| D     | 0.01 | 0.01 | 0.98    |
| E     | 0.60 | 0.01 | 0.39    |

The MgAPSO molecular sieves of U.S. Pat. No. 4,758,419 have a framework structure of $MgO_2^{-2}$, $AlO_2^{-}$, $PO_2^{+}$, and $SiO_2$ tetrahedral units having an empirical chemical composition on an anhydrous basis expressed by the formula:

mR: $(Mg_wAl_xP_ySi_z)O_2$ wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

|       | Mole Fraction |      |         |
| Point | x    | y    | (z + w) |
| ----- | ---- | ---- | ------- |
| A     | 0.60 | 0.38 | 0.02    |
| B     | 0.39 | 0.59 | 0.02    |
| C     | 0.01 | 0.60 | 0.39    |
| D     | 0.01 | 0.01 | 0.98    |
| E     | 0.60 | 0.01 | 0.39    |

The MnAPSO molecular sieves of U.S. Pat. No. 4,793,833 have a framework structure of $MnO_2^{-2}$, $AlO_2^{-}$, $PO_2^{+}$, and $SiO_2$ tetrahedral units having an empirical chemical composition on an anhydrous basis expressed by the formula:

mR: $(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

|       | Mole Fraction |      |         |
| Point | x    | y    | (z + w) |
| ----- | ---- | ---- | ------- |
| A     | 0.60 | 0.38 | 0.02    |
| B     | 0.38 | 0.60 | 0.02    |
| C     | 0.01 | 0.60 | 0.39    |
| D     | 0.01 | 0.01 | 0.98    |
| E     | 0.60 | 0.01 | 0.39    |

It is within the scope of the invention that the catalyst comprises two or more NZMSs. Preferably the NZMSs are as a multi-compositional, multi-phase composite having contiguous phases, a common crystal framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. In a highly preferred embodiment the layered catalyst comprises a crystalline aluminophosphate of U.S. Pat. No. 4,310,440 and a SAPO, especially ALPO-11 and SAPO-11.

The NZMS preferably is combined with a binder for convenient formation of catalyst particles. The binder should be porous, adsorptive support having a surface area of about 25 to about 500 m$^2$/g, uniform in composition and relatively refractory to the conditions utilized in the hydrocarbon conversion process. By the term "uniform in composition," it is meant that the support be unlayered, have no concentration gradients of the species inherent to its composition, and be completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (6) combinations of materials from one or more of these groups.

For some uses, e.g. for olefin isomerization, the catalyst preferably is substantially free of a hydrogenation promoter such as a Group VIII metal which would result in economically significant losses of olefins to paraffins through hydrogenation. The preferred catalyst contains less than 100 mass parts per million (ppm) on an elemental basis of hydrogenation promoter, and optimally less than about 10 mass ppm. It is especially preferred that the catalyst be substantially free of platinum and palladium.

The catalyst of the present invention may contain a halogen component. The halogen component may be either fluorine, chlorine, bromine or iodine or mixtures thereof. Chlorine is the preferred halogen component. The optional halogen component is generally present in a combined state with the inorganic-oxide support and preferably is well dispersed throughout the catalyst.

The catalytic composite optionally may contain other metal components in addition to or in the absence of a platinum-group metal. Such components may include, for example, one or more of rhenium, tin, germanium, lead, gallium, indium, cobalt, nickel, manganese, chromium, molybdenum, tungsten, zinc, dysprosium, thallium, uranium. The catalyst also may incorporate one or more of the alkali metals or alkaline earth metals. Catalytically active amounts of such metal components may be incorporated into the catalyst composite in any suitable manner known in the art.

The catalyst composite may be dried at a temperature of from about 100° to about 320° C. for a period of from about 2 to about 24 or more hours and calcined at a temperature of from 400° to about 650° C. in an air atmosphere for a period of from about 0.1 to about 10 hours.

If elemental metals are present in the finished composite, the calcined composite may be subjected to a substantially water-free reduction step to ensure a uniform and finely divided dispersion of the metal components. The reducing agent, preferably hydrogen containing less than 20 vol. ppm water, contacts the catalyst at conditions, including a temperature of from about 200°–650° C. for a period of about 0.5–10 hours, effective to reduce substantially all of the relevant metals. The reduced composite optionally may be subjected to a presulfiding operation by suitable techniques known in the art before undergoing controlled carbon deposition.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art recognize, which are within the spirit of the invention.

EXAMPLE I

A reference butene-isomerization pilot-plant run "R" was performed as a control for subsequent testing of the effect of activity moderation. All of the pilot-plant tests were performed on a butene-isomerization feedstock blended to contain normal butenes and butane in a molar ratio of 2 to 1. The catalyst used in the comparative tests was a 65%-SAPO-11 (silicoaluminophosphate), 35% silica extrudate, containing substantially no hydrogenation metals; SAPO-11 prepared according to the teachings of U.S. Pat. No. 4,440,871 was washed with nitric acid and extruded with Ludox. Isomerization tests were carried out at 455° C., mass hourly space velocity of 2.5 hr$^{-1}$, pressure of 2.4 atmospheres absolute, and ratio of hydrogen to hydrocarbons ($H_2$/HC mol ratio) of 0.2. The cycle length was set to obtain an end-of-run conversion of butenes of about 35% over a period of about three days.

Figure 2:
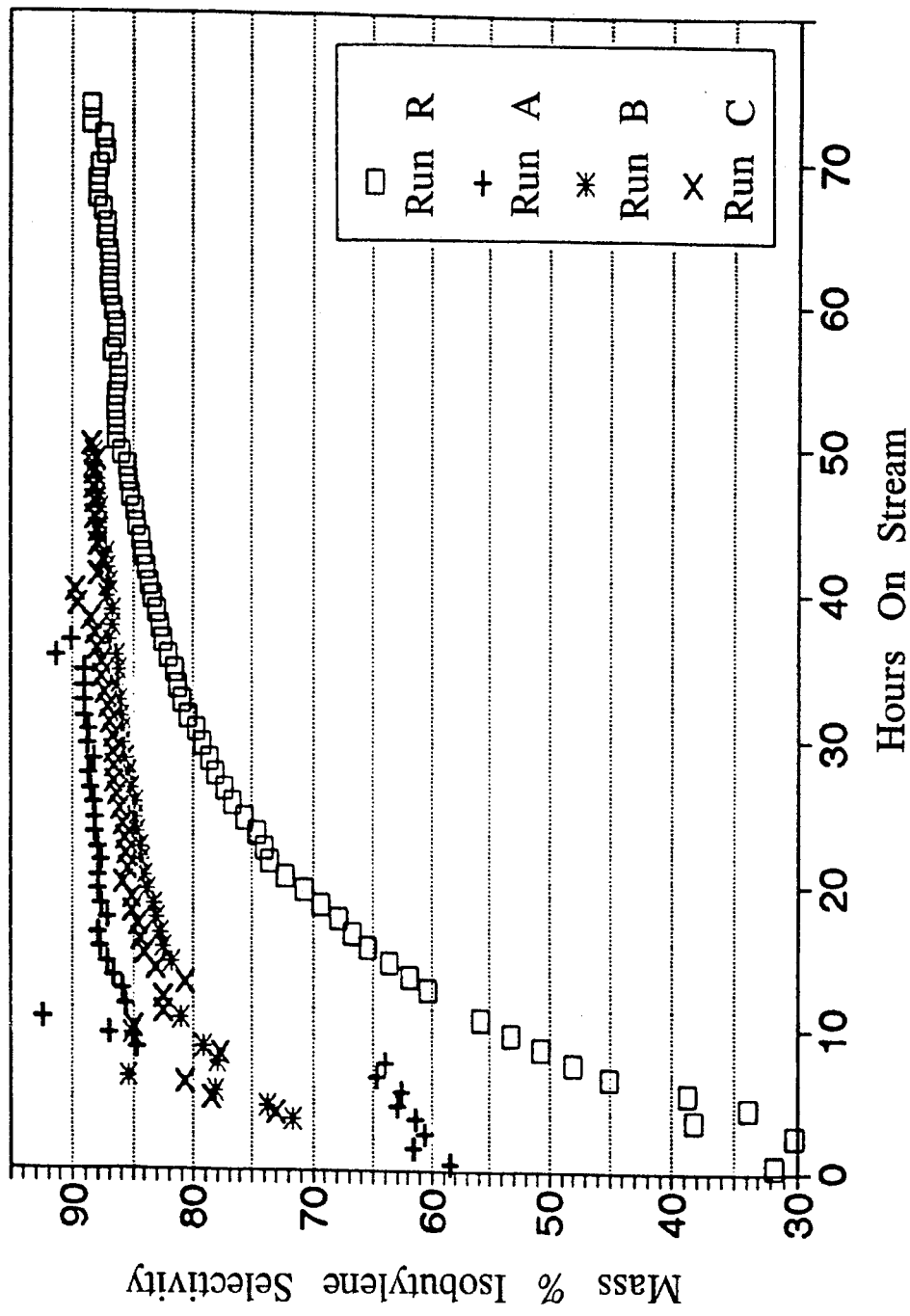
FIG. 2 shows selectivity to isobutene product vs. time on-stream for isomerization using catalysts with and without activity moderation.

The conversion history of the reference run R is shown in FIG. 1. FIG. 2 reviews the selectivity history of n-butene converted to isobutene over the duration of the run.

EXAMPLE II

The 65%-SAPO-11 catalyst of Example I was activity-moderated by controlled carbon deposition by processing the 2/1 butenes/butane feedstock of Example I at 455° C., mass hourly space velocity of 2.5 hr$^{-1}$, and pressure of 8 atmospheres absolute in the absence of hydrogen. The objective of the carbon deposition was to moderate its activity the catalyst by restricting initial conversion of butenes in subsequent isomerization to about 50%. In a first pilot-plant run A, the controlled carbon deposition was effected for about 4 hours, and subsequent conversion was 46%. In two later runs B and C, therefore, carbon deposition was effected for about 3 hours to approach the 50%-conversion target.

The catalysts subsequently were tested to ascertain butene-isomerization performance on the same feedstock as used in the carbon-deposition step. The isomerization tests for each of runs A–C were carried out at 455° C., mass hourly space velocity of 2.5 hr$^{-1}$, and pressure of 2.4 atmospheres absolute. Hydrogen was introduced into the pilot plant to effect a ratio of hydrogen to hydrocarbons ($H_2$/HC mol ratio) of 0.2. The cycle length was set to obtain an end-of-run conversion of butenes of about 35% and amounted to up to about 48 hours.

Conversion of n-butenes vs. time on-stream for each of the runs is shown in FIG. 1. Initial conversion using the catalysts which were activity-moderated by controlled carbon deposition, other than the 46% for the catalyst which was activity-moderated by controlled carbon deposition for four hours, was moderated to about 50% compared to a much higher value for the non-activity-moderated catalyst.

Selectivity, measured as mass % isobutene product relative to n-butenes converted, is shown in FIG. 2. The catalysts with controlled carbon deposition show a clear selectivity advantage in the earlier stages of the respective runs.

Relative performance with and without activity moderation is further compared with reference to the following parameters:

Selectivity to 35% conversion

Average selectivity from the start of run to the point at which 35% conversion, representing the expected minimum economic conversion level, is reached % hours on stream>80% selectivity Proportion of the time to 35% conversion that better than 80% selectivity is achieved.

|  | Reference | Activity-Moderated | | |
| --- | --- | --- | --- | --- |
|  | R | A | B | C |
| Selectivity to 35% conversion | 75% | 88% | 85% | 85% |
| % hours on stream >80% | 42% | 74% | 80% | 87% |

-continued

|  | Reference | Activity-Moderated | | |
|---|---|---|---|---|
|  | R | A | B | C |
| selectivity | | | | |

The activity-moderated catalysts A, B and C of the invention achieve superior selectivity relative to the reference. Further, the proportion of the time on-stream at which greater than 80% selectivity is achieved is substantially enhanced by activity moderation.

EXAMPLE III

A 65% SAPO-11 catalyst prepared according to Example I was activity-moderated by controlled carbon deposition. Feed was a 1 to 1 molar ratio of normal butene and butanes, which was processed over the catalyst in a pilot plant at 455° C., mass hourly space velocity of 2.5 hr$^{-1}$ and a pressure of 8 atmospheres absolute for a period of three hours. The top half and the bottom half of the catalyst were analyzed separately for carbon content, with the following results:

| Top half | 3.0 mass % |
|---|---|
| Bottom half | 2.9 mass % |

Thus, there was no substantial gradient in carbon content through the catalyst bed.

EXAMPLE IV

A catalyst sample prepared according to Example I was tested for the effect of controlled carbon deposition on a high-space-velocity butene-isomerization operation. The butene-containing feedstock was as described in Example I.

Activity moderation was effected by processing the feedstock at 455° C. and pressure of 5 atmospheres absolute for 10–20 minutes in the absence of hydrogen. The catalyst subsequently was tested to ascertain butene-isomerization performance on the same feedstock as used in the activity-moderation step, and this performance was compared to a control isomerization test without activity moderation. The isomerization tests were carried out at 455° C., mass hourly space velocity of 20 hr$^{-1}$, and pressure of 2 atmospheres absolute. Hydrogen was introduced into the pilot plant to effect a ratio of hydrogen to hydrocarbons (H$_2$/HC mol ratio) of 0.2.

The pilot-plant test runs extended over a period wherein butenes conversion declined from about 45% to 30%. The duration of this period for the catalyst was about 35 hours, compared to about 9 hours for the catalyst without precoking. The catalyst thus demonstrated nearly four times the catalyst life at the optimal conversion range. Acceptable life is achieved by activity moderation enabling operation at lower space velocity with acceptable selectivity. Selectivities to isobutene were similar for the two runs at high conversions, and, although gas-liquid chromatograph uncertainties precluded a reliable data plot favored the precoked catalyst at low conversions.

We claim:

1. A process for the isomerization of olefins, comprising one or both of butenes and pentenes, which comprises contacting an olefin-containing feedstock in the presence of free hydrogen in a molar ratio to feedstock of about 0.01 to 5 at isomerization conditions with a catalyst containing at least one non-zeolitic molecular sieve (NZMS) and having the substantial absence of Group VIII metals to provide a product containing a greater concentration of one or more of the group consisting of isobutenes and isopentenes than in the feedstock, wherein the NZMS catalyst has been activity-moderated by controlled carbon deposition sequentially in the same equipment without an intervening step prior to its use for olefin isomerization by contacting the catalyst with the feedstock in the absence of free hydrogen for a time of from about 0.5 to 6 hours at activity-moderation conditions including a temperature of from about 200° to 600° C. to effect a catalyst carbon content of from about 0.1 to 20 mass %.

2. The process of claim 1 wherein the carbon content is from about 0.5 to 5 mass %.

3. The process of claim 1 wherein the NZMS is selected from the group consisting of SAPOs, FAPOs, CoAPSOs, MnAPSOs, MgAPSOs and mixtures thereof.

4. The process of claim 1 wherein the NZMS is SAPO-11.

5. The process of claim 1 wherein the catalyst comprises an inorganic oxide matrix component.

6. The process of claim 1 wherein the isomerization conditions comprise a temperature of from about 200° to 600° C., a pressure of from about atmospheric to 50 atmospheres, and a weight hourly space velocity of from about 0.5 to 100 hr$^{-1}$.

7. The process of claim 1 wherein the product is subjected to etherification to produce one or more ethers from the group consisting of methyl t-butyl ether, ethyl t-butyl ether, and methyl t-amyl ether.

8. In a process for the isomerization of butenes, which comprises contacting a butene-containing feedstock in the presence of free hydrogen in a molar ratio to feedstock of about 0.01 to 5 at isomerization conditions with a catalyst containing at lest one non-zeolitic molecular sieve (NZMS) and having the substantial absence of Group VIII metals to provide a product containing a greater concentration of isobutenes than in the feedstock, wherein the catalyst has been activity-moderated by controlled carbon deposition sequentially in the same equipment without an intervening step prior to its use for isomerization by contacting the catalyst with the feedstock in the absence of free hydrogen for a time of from about 0.5 to 6 hours at activity-moderation conditions including a temperature of from about 200° to 600° C. to effect a catalyst carbon content of from about 0.1 to 20 mass %.

9. In a process for the isomerization of pentenes, which comprises contacting a pentene-containing feedstock in the presence of free hydrogen in a molar ratio to feedstock of about 0.01 to 5 at isomerization conditions with a catalyst containing at least one non-zeolitic molecular sieve (NZMS) to provide a product containing a greater concentration of isopentenes than in the feedstock, wherein the catalyst has been activity-moderated by controlled carbon deposition sequentially in the same equipment without an intervening step prior to its use for olefin isomerization by contacting the catalyst with the feedstock in the absence of free hydrogen for a time of from about 0.5 to 6 hours at activity-moderation conditions including a temperature of from about 200° to 600° C. to effect a catalyst carbon content of from about 0.1 to 20 mass %.

* * * * *